United States Patent
Wang et al.

(10) Patent No.: US 11,219,358 B2
(45) Date of Patent: Jan. 11, 2022

(54) METHOD AND APPARATUS FOR DETECTING MISSED AREAS DURING ENDOSCOPY

(71) Applicant: CAPSOVISION, Inc., Saratoga, CA (US)

(72) Inventors: Kang-Huai Wang, Saratoga, CA (US);
Chenyu Wu, Sunnyvale, CA (US);
Mark Hadley, Los Altos, CA (US);
Gordon C. Wilson, San Francisco, CA (US)

(73) Assignee: Capso Vision Inc., Saratoga, CA (US)

( * ) Notice: Subject to any disclaimer, the term of this patent is extended or adjusted under 35 U.S.C. 154(b) by 0 days.

(21) Appl. No.: 17/177,167

(22) Filed: Feb. 16, 2021

(65) Prior Publication Data

US 2021/0267441 A1    Sep. 2, 2021

Related U.S. Application Data

(63) Continuation-in-part of application No. 16/806,286, filed on Mar. 2, 2020.

(60) Provisional application No. 62/987,876, filed on Mar. 11, 2020.

(51) Int. Cl.
*A61B 1/04* (2006.01)
*A61B 1/00* (2006.01)
*A61B 1/01* (2006.01)

(52) U.S. Cl.
CPC .......... *A61B 1/041* (2013.01); *A61B 1/00009* (2013.01); *A61B 1/00045* (2013.01); *A61B 1/00188* (2013.01); *A61B 1/01* (2013.01); *A61B 2562/0219* (2013.01)

(58) Field of Classification Search
CPC .................................. A61B 1/041; A61B 1/01
USPC .......................................................... 348/65
See application file for complete search history.

(56) References Cited

U.S. PATENT DOCUMENTS

| | | | |
|---|---|---|---|
| 9,936,151 B2 | 4/2018 | Wang | |
| 2006/0195014 A1* | 8/2006 | Seibel | A61B 1/0661 600/102 |
| 2007/0161854 A1* | 7/2007 | Alamaro | A61B 1/00193 600/109 |
| 2011/0032347 A1* | 2/2011 | Lacey | A61B 5/065 348/68 |
| 2011/0092825 A1* | 4/2011 | Gopinathan | G16H 40/67 600/483 |
| 2017/0367560 A1* | 12/2017 | Shiraki | A61B 1/00009 |

(Continued)

*Primary Examiner* — Amir Shahnami
(74) *Attorney, Agent, or Firm* — Blairtech Solution LLC

(57) ABSTRACT

A method of processing images captured using an endoscope comprising a camera is disclosed. According to this method, regular images captured by the camera are received while the endoscope travels through a human gastrointestinal (GI) tract. The regular images are mosaicked to determine any missed or insufficiently imaged area in a section of the human GI tract already travelled by the endoscope. If any missed or insufficiently imaged area is detected, information regarding any missed or insufficiently imaged area is provided. When a target area in the regular images is lack of parallax, the target area is determined as one missed area and an edge corresponding to a structure of the human lumen is highlighted. For a capsule endoscope, the endoscope can be configured to be controlled or steered to move so as to re-image the missed or insufficiently imaged area.

28 Claims, 2 Drawing Sheets

(56) References Cited

U.S. PATENT DOCUMENTS

2020/0387706 A1\* 12/2020 Zur .................... G06K 9/6271
2021/0195102 A1\* 6/2021 Yangdai ............ H04N 5/23232

\* cited by examiner

METHOD AND APPARATUS FOR DETECTING MISSED AREAS DURING ENDOSCOPY

CROSS REFERENCE TO RELATED APPLICATIONS

The present invention is a non-provisional application of and claims priority to U.S. Provisional Patent Application Ser. No. 62/987,876, filed on Mar. 11, 2020, which is a continuation-in-part application of and claims priority to U.S. patent application Ser. No. 16/806,286, filed on Mar. 2, 2020. The present invention is also related to U.S. Pat. No. 9,936,151, granted on Apr. 3, 2018. The U.S. Patent Application, U.S. Provisional Patent Application and U.S. Patent are hereby incorporated by reference in their entireties.

FIELD OF THE INVENTION

The present invention relates to image/video processing for image sequences of human gastrointestinal (GI) tract captured using an endoscope. In particular, the present invention relates to detecting missed areas or insufficiently imaged area of the GI tract and providing feedback to the medical professional conducting the endoscopy procedure or providing movement control to an autonomous capsule endoscope.

BACKGROUND AND RELATED ART

Devices for imaging body cavities or passages in vivo are known in the art and include endoscopes and autonomous encapsulated cameras. Endoscopes are flexible tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. Today, colonoscopy is still the gold standard for colon screening to prevent colon cancer. However colonoscopy is not perfect and sometimes the polyp may be missed.

There are two major types that polyps may be missed. In one type, the doctor visualizes the area where a polyp may exist, but fails to recognize it is a polyp for various reasons. Sometimes, the polyp appearance may be subtle and not easy to be discerned from the background colon mucosa. For the other type, some areas may be missed, i.e., not examined, during colonoscopy due to the inadequate skill or the fatigue of the colonoscopist. This may also be combined with the difficulty to maneuver the flexible tube through a convoluted and torturous colon.

For the first type of problem, there have been various studies and even products using artificial intelligence to help doctors, especially the beginner, to recognize polyp. Such system can provide notices to a doctor to highlight on the display to indicate where the polyp may be. For example, in a published article by Peter Klare, et al. ("Automated polyp detection in the colorectum: a prospective study", *Gastrointestinal Endoscopy*, Vol. 89, No. 3, 2019, pp. 576-82), an application of a real-time automated polyp detection software (APDS) under routine colonoscopy conditions has been disclosed. They have concluded that computer-assisted automated low-delay polyp detection is feasible during real-time colonoscopy. In another article by Daniela Guerrero Vinsard, et al. ("Quality assurance of computer-aided detection and diagnosis in colonoscopy", *Gastrointestinal Endoscopy*, Vol. 90, No. 1, 2019; pp. 55-63), they reviewed both contributions and limitations in recent machine-learning-based CADe and/or CADx (computer-aided detection and diagnosis) colonoscopy studies. They concluded that once the efficacy and reproducibility of AI systems are validated in rigorously designed trials, the machine-learning-based CADe and/or CADx may have a significant impact on colonoscopy practice.

While various studies have been devoted to addressing the first-type problem, the second-type problem (i.e., missed area or insufficiently imaged area during colonoscopy) is yet to be resolved. Accordingly, the present invention is intended to deal with the second-type problem. In particular, the present invention is intended to develop methods that can detect the missed area or insufficiently imaged area in real time or near real-time to assist the colonoscopy procedure. The missed area issue may also happen to capsule endoscope. The detection of the missed area or insufficiently imaged area will be performed using the processing capability of an examination or display station to achieve real-time or near real-time detection. Accordingly, with the help of this invention, the probability of missed area or insufficiently imaged area can be eliminated or reduced.

BRIEF SUMMARY OF THE INVENTION

A method of processing images captured using an endoscope comprising a camera is disclosed. According to this method, regular images captured by the camera are received while the endoscope travels through a human gastrointestinal (GI) tract. The regular images are mosaicked to determine any missed or insufficiently imaged area in a section of the human GI tract already travelled by the endoscope. If any missed or insufficiently imaged area is detected, information regarding any missed or insufficiently imaged area is provided.

The method may further comprise receiving structured light images associated with the regular images from the camera and deriving distance information of the regular images based on the structured light images, where the structured light images are captured by the camera while the endoscope travels through the human GI tract. The distance information of the regular images can be used to assist said mosaicking the regular images. The lumen view does not have many sharp edges or features for reliable registration. Therefore, the distance information facilitates the possibility of correct mosaicking process. The regular images are normalized according to the distance information of the regular images and optical magnification information to facilitate said mosaicking the regular images.

In one embodiment, the distance information is used to determine whether a target area in one regular image is out of focus or not and if the target area is out of focus in all regular images covering the target area, the target area is determined as one missed or insufficiently imaged area.

In another embodiment, the endoscope further comprises a motion sensing device to measure camera motion inside the human GI tract. For example, the motion sensing device corresponds to an accelerometer or a gyrator. The motion sensing device can be used to determine camera movement, camera trajectory, camera orientation or any combination thereof. Said mosaicking the regular images can be performed in a space based on the camera trajectory.

In one embodiment, said providing the information regarding any missed or insufficiently imaged area to the operator comprises displaying the regular images with highlight on any missed or insufficiently imaged area. In another embodiment, the method further comprises generating a 2D or 3D mosaicked image and displaying the 2D or 3D mosaicked image on a display device with any missed or insufficiently imaged area highlighted.

In one embodiment, the method may further comprise generating a 2D or 3D mosaicked image and storing the 2D or 3D mosaicked image. For a tethered endoscope, the information of the 2D or 3D mosaicked image stored is used by the operator during withdraw process of the endoscope to re-image any missed or insufficiently imaged area. Alternatively the 2D and 3D mosaicking can be built during the withdrawal process. The information of the 2D or 3D mosaicked image stored may also be used in a subsequent colonoscopy of a same patient.

In one embodiment, for a capsule endoscope, the endoscope is configured to be controlled or steered to move so as to re-image other side of the edge.

In one embodiment, a target area in the regular images is lack of parallax, the target area is determined as one missed or insufficiently imaged area. For a capsule endoscope, the endoscope is configured to be controlled or steered to move so as to re-image other side of the edge. In another embodiment, a target area in the regular images is lack of a surface area in mosaicked result, the target area is determined as one missed or insufficiently imaged area. In one embodiment, when a target area in the regular images is lack of parallax, the target area is determined as one missed area and a related structure in the human lumen is highlighted. For a capsule endoscope, the endoscope is configured to be controlled or steered to move so as to re-image the target area In one embodiment, the method may further comprise deriving camera position, camera movement, camera orientation or a combination thereof inside the human lumen by using motion estimation based on the regular images. In another embodiment, the motion estimation is derived using the distance information from structure light image.

DETAILED DESCRIPTION OF THE INVENTION

Figure 1A:
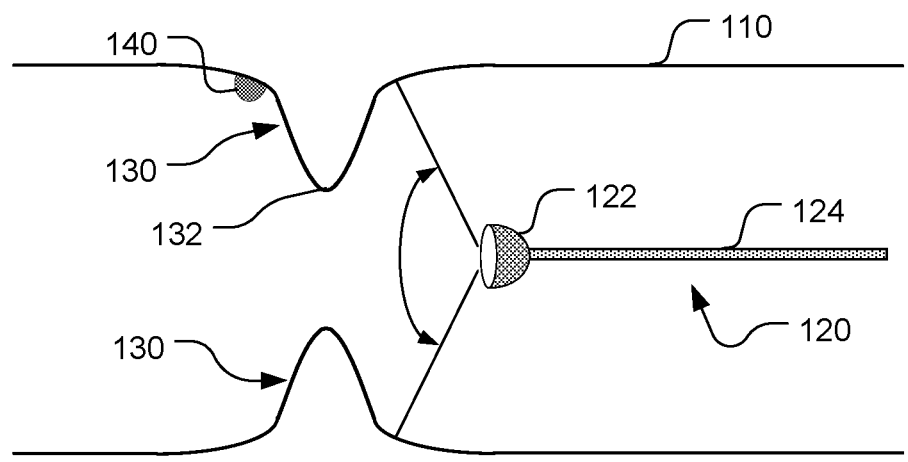
FIG. 1A illustrates an exemplary scenario, where there is an edge corresponding to a fold of the colon and a polyp at the bottom of the fold, where the polyp may be easily missed since it is blocked by the fold.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. References throughout this specification to "one embodiment," "an embodiment," or similar language mean that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

A colonoscopy enables your doctor to examine the lining of your rectum, colon (large intestine) and the lowest part of the small intestine (known as the ileum) for any abnormalities. During colonoscopy, an endoscope is inserted from the anus and then slowly advanced into the rectum, colon and ileum. The colonoscopy is intended to cover all the surface areas of the portion of the human gastrointestinal (GI) tract travelled by the colonoscope. However, the colonoscope has a limited field of view (FOV). In addition, due to various difficult conditions in the GI tract, such as sharp bends, folds, twists and turns in the colon, they present a great challenge to maneuver the endoscope for imaging the GI tract with complete coverage.

In order to deal with the missed area problem, the present invention discloses techniques based on picture mosaicking to identify possible missed areas or ill-imaged areas (also termed as insufficiently imaged areas) during the colonoscopy. The insufficiently imaged areas refer to areas that do not provide sufficient image quality for picture mosaicking. The insufficiently imaged areas may due to objects being out of focus, objects being partially occluded, etc. The picture mosaicking may correspond to a 3D mosaicking (i.e., 3D registration) or 2D mosaicking (i.e., image stitching). If the missed or insufficiently imaged area can be timely detected for the section imaged by the endoscope, it is possible to alert the colonoscopist about the missed area so that corrective action may be taken. The stitched image can provide a panoramic view of the lumen. Accordingly, the stitched image is also referred as a panorama image in this disclosure. In order to make timely alert to the colonoscopist, the detection of missed of insufficiently imaged area has to be done in real time or near real time. For example, the detection has to be completed in few seconds or less. The key idea behind the present invention is that the colon is a closed tract so that the images taken from the colonoscope can be stitched the imaged area to form a closed tract without any missed of insufficiently imaged area. If there is any missed or insufficiently imaged area, it implies that there is an area on the tract un-imaged or ill-imaged.

In order to alert the colonoscopist about a missed area, one embodiment of the present invention will display the stitched image with the un-imaged area highlighted. The highlight of the missed area can be in the form of outline of the missed area. In another example, the highlight of the missed area can be in the form of overlay color. In another embodiment, an audible sound or other notifying signal may be provided to the colonoscopist.

Various missed area detection methods are disclosed in the present invention. In one embodiment, if an area in the captured image is lack of parallax, the area is considered as a candidate for missed area or insufficiently imaged area. As known in the field, parallax is a displacement or difference in the apparent position of an object viewed along two different lines of sight. The parallax is measured by the angle or semi-angle of inclination between those two lines. Due to foreshortening, nearby objects show a larger parallax than farther objects when observed from different positions. Therefore, the parallax has been used to determine distances in various applications. According to one embodiment of the present invention, picture mosaicking identifies a corresponding target area in multiple captured images and stitches the corresponding target area using the multiple captured images. If such parallax is not available for a corresponding target area, the corresponding target area is determined as a candidate for missed area or insufficiently imaged area.

FIG. 1A illustrates an exemplary scenario, where there is an edge 132 corresponding to a fold 130 of the colon 110 and a polyp 140 at the bottom of the fold as shown in FIG. 1. The polyp may be easily missed since it is blocked by the fold. The polyp may be visible by the camera 122 when the camera just passed the fold. As shown in FIG. 1A, the endoscope 120 comprises a camera 122 and a flexible tube 124. In this case, the area associated with the polyp will only be seen from one perspective angle. According to the embodiment, the area around the polyp is lack of parallax and is identified as a missed or insufficiently imaged area. Accordingly, the area should be highlighted. For example the edge is highlighted, or the colonoscopist is notified of such an occluded area. In one embodiment, the endoscope is configured to be controlled or steered to move so as to re-image the missed or insufficiently imaged area. In one embodiment, when a target area in the regular images is lack of parallax, the target area is determined as one missed area and a related structure in the human lumen is highlighted. For a capsule endoscope, \ the endoscope is configured to be controlled or steered to move so as to re-image the target area.

Figure 1B:
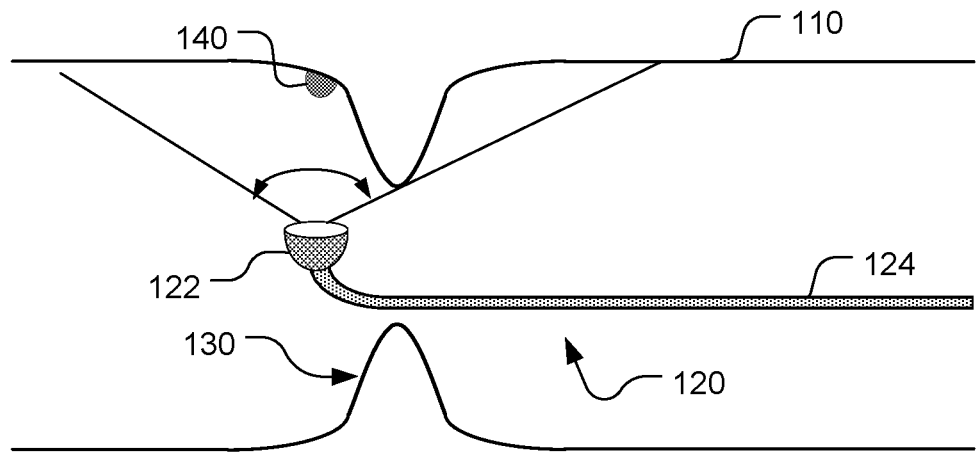
FIG. 1B illustrates an exemplary scenario, where the camera is angled to get a good look at the missed or insufficiently imaged area.

For the condition described in FIG. 1A, the other side of the edge may not be adequately imaged. If there exists a substantial edge (e.g. edge 132), a panorama image may not be stitched showing the two sides of the edge to avoid the occluded area including the polyp 140. If an area is missing in this panorama image, then the colonoscopist should be notified. Furthermore, the way it is notified can be different from a missing area not resulting from the edge and the lack of a parallax associated with the occluded area. In 3D mosaicking, this occluded area should manifest as the lack of a surface area in the mosaicked result. In another embodiment, motion estimation in the space can be used to provide the camera position, movement and orientation. If the other side of the edge is not viewed, such as the case shown in FIG. 1B, the colonoscopist can be notified. In another embodiment, in the case that the movement and orientation can be available from a motion sensing devices, if the other side of the edge is not examined, the colonoscopist can be notified. The colonoscopist can then adjust the camera angle to get a good look at the missed or insufficiently imaged area as shown in FIG. 1B.

For the intended application, in addition to viewing the captured images and being aware of possible missed or insufficiently imaged area, it is also important to let the colonoscopist know the location or relative location of the camera. Therefore, when there is a need to maneuver the camera to cover a missed or insufficiently imaged area, the colonoscopist can be timely informed about the needed movement. In order to determine the camera location and/or orientation inside the GI tract, in one embodiment of the present invention, the colonoscope is further be equipped with a motion sensing device, such as an accelerometer or gyrator. Therefore, the movement and the trajectory of the camera as well as its orientation can be determined so that the doctor can be better informed of the colon structure and relative position between the camera and the surrounding GI tract associated with the image being displayed. In one embodiment the stitched image could be formed in the space based on the trajectory of the camera movement.

In another embodiment, the endoscope can be equipped with structured lights to capture regular images along with structured light images. The structured light images (SLIs) can be used to derive the distance of the different areas in the image so that the stitching can be more accurate by using the 3D information of the imaged areas. Furthermore, with the more accurate starting point in iteration of the stitching process, the stitched image can avoid falling into local minimum. In U.S. Pat. No. 9,936,151 that is being incorporated by reference, a camera equipped with a regular light and structured light is disclosed to capture both regular images and structured light images using the same image sensor. The structured light images and corresponding regular images are captured temporally close so that the motion in between is expected to be small. Accordingly, the distance information derived from the structured light image correlates highly with the regular image. Details regarding the camera design with SLI capture capability are disclosed in U.S. Pat. No. 9,936,151.

These 2D or 3D mosaicked structure may help the endoscopy procedure. For example, the 2D or 3D mosaicked structure maybe by a different colonoscopist so that the anatomy information can help the colonoscopist to steer within the lumen. This concept, as well as the other concepts in the invention, could be applied to GI tracts or organ or other areas of the body, such as bladder.

In addition to the fact that the lumen surface lacks the sharp edges and features to facilitate registration, some studies (e.g., J. Davis, "Mosaics of scenes with moving objects," *Proceedings. 1998 IEEE Computer Society Conference on Computer Vision and Pattern Recognition* (Cat. No. 98CB36231), Santa Barbara, Calif., 1998, pp. 354-360) in the field of picture mosaicking have found that the close distance between object and camera makes the stitching more difficult. Therefore, the distance information is extremely important for GI images since the distance is typically very close. In one embodiment, during the operation of the colonoscopy, only regular images are displayed on the screen and structured light images are not displayed. However, the structured light images can be fed through the computer or a processor for calculating distance information of the regular image. In one embodiment, the regular images are normalized according to the distance information and optical magnification information to facilitate stitching. In another embodiment, the stitched 2D or 3D structure can be displayed in real time or near real time. In yet another embodiment the missed area is highlighted on the stitched 2D or 3D structure. The stitched image can be shown in the form of a surface of a tract. The stitching algorithm can be rigid or non-rigid to take into account some movement of the bowel during the colonoscopy.

In the case of colonoscopy equipped with structured light to capture SLIs and deriving the distance information, the regular image with areas out of focus can be determined. During stitching, the overlapped area should be dominated by the pixels properly focused. If there is an area where all the images covering this area are all out of focus for this area, then this area is a candidate for ill-imaged area. This area should be highlighted or a notice should be provided to the colonoscopist.

In another embodiment, the colonoscope can be equipped with a motion sensing device (e.g. accelerator or gyrator, etc.) to determine its movement and the trajectory of the camera as well as one or more structured lights to capture SLIs and derive corresponding distance information. By combining the structured light and the motion sensing device, an accurate 3D structure of the GI tract can be built in real time. Based on the accurate 3D structure of the GI tract, the colonoscopy system can be configured to highlight any un-examined area and to alert the doctor of the area un-examined. Furthermore, the colonoscopy system can be configured to assist the doctor during colonoscopy by knowing physiological topology and the pathological topology when existing. Alternatively, these information can be recorded and used later.

This invention can also be used in other GI tracts, such as stomach, or non-GI areas such as bladder.

In addition to tethered endoscope, a capsule endoscope can also benefit from the invention for detecting missed area. For the system where the capsule can be controlled or steered to move, such as a mechanized capsule or a magnetic controlled capsule, the real time detection of missed area can be used to cause the motion of the capsule in such a way that the capsule may re-image the missed area. Sometimes, although the capsule cannot be controlled, the pose position of the subject (e.g., a patient) may be changed to cause the capsule to image the desirable region. The missed area information can be utilized to provide guide to pose the correct position of the subject. On the other hand, the missed area information may provide valuable information about the procedure to a clinician. In another embodiment, the missed area information can be provided for programming the capsule in such a way that the missed area can be avoided or reduced.

In another embodiment, with mosaicking performed correctly, the redundant overlapped areas can be removed. Based on the information of aggregated redundant areas, it can provide the information regarding whether the frame rate can be reduced in order to conserve energy and other resources of the capsule. On the other hand, it can provide the information regarding whether to increase the frame rate in order to avoid or reduce the missed areas. The abundance of the redundant areas also indicates an area has been amply imaged.

Figure 2:
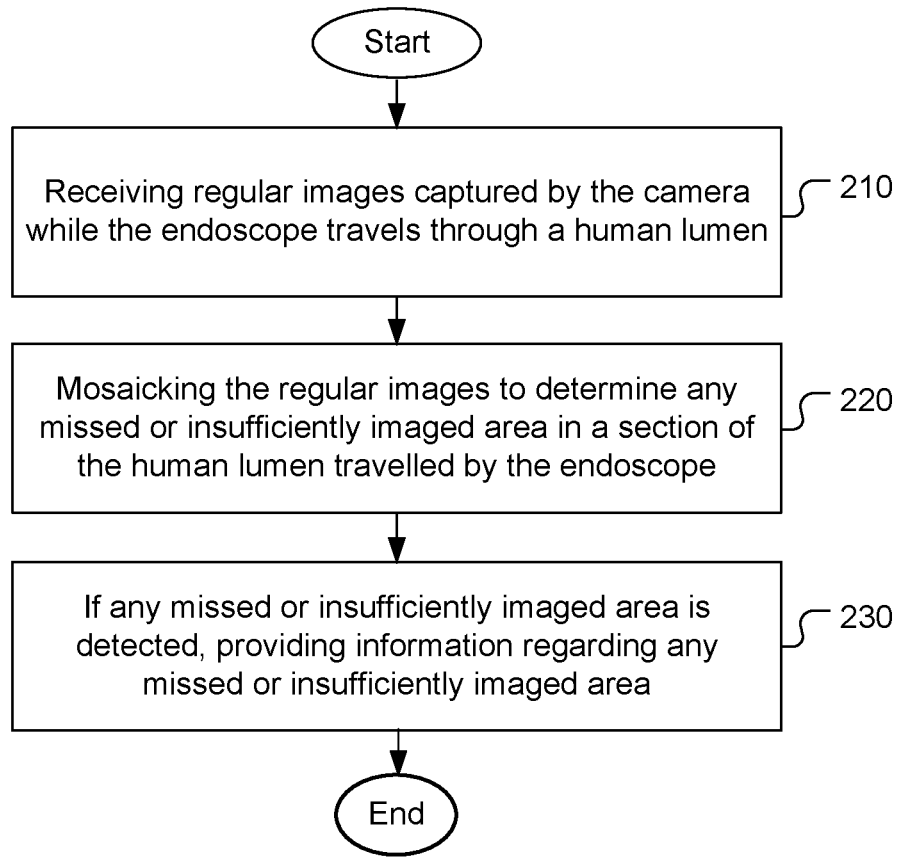
FIG. 2 illustrates an exemplary flowchart for processing images captured using an endoscope comprising a camera according to an embodiment of the present invention, where a missed or insufficiently imaged area is detected.

FIG. 2 illustrates an exemplary flowchart for processing images captured using an endoscope comprising a camera according to an embodiment of the present invention, where a missed or insufficiently imaged area is detected. According to this method, regular images captured by the camera are received while the endoscope travels through a human lumen in step 210. The regular images are mosaicked to determine any missed or insufficiently imaged area in a section of the human lumen travelled by the endoscope in step 220. If any missed or insufficiently imaged area is detected, information regarding any missed or insufficiently imaged area is provided in step 230.

The method may be implemented in software for execution by various types of processors. For example, the processor may correspond a computer associated with the colonoscopy examination station or a workstation coupled to receive images from the colonoscope.

The above description is presented to enable a person of ordinary skill in the art to practice the present invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the above detailed description, various specific details are illustrated in order to provide a thorough understanding of the present invention. Nevertheless, it will be understood by those skilled in the art that the present invention may be practiced.

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of processing images captured using an endoscope comprising a camera, the method comprising:
   receiving regular images captured by the camera while the endoscope travels through a human lumen;
   mosaicking the regular images into a mosaicked image to determine any missed area in a section of the human lumen travelled by the endoscope, wherein distance information of the regular images is used to assist said mosaicking the regular images, and the distance information is derived based on structured light images associated with the regular images, and wherein the regular images are normalized according to the distance information of the regular images and optical magnification information to facilitate said mosaicking the regular images; and
   if any missed area is detected, providing information regarding any missed area.

2. The method of claim 1, wherein the distance information is used to determine whether a target area in one regular image is out of focus or not and if the target area is out of focus in all regular images covering the target area, information of the target area is provided.

3. The method of claim 1, wherein the endoscope further comprises a motion sensing device to measure camera motion inside the human lumen.

4. The method of claim 3, wherein the motion sensing device corresponds to an accelerometer or a gyrator.

5. The method of claim 3, wherein the motion sensing device is used to determine camera movement, camera trajectory, camera orientation or any combination thereof.

6. The method of claim 5, wherein said mosaicking the regular images is performed in a space based on the camera trajectory.

7. The method of claim 1, wherein a target area in the regular images is lack of a surface area in the mosaicked image, the target area is determined as one missed area.

8. The method of claim 1, wherein said providing the information regarding any missed area comprises displaying the mosaicked image with highlight on any missed area.

9. The method of claim 1 further comprising generating a 2D or 3D mosaicked image and displaying the 2D or 3D mosaicked image on a display device with any missed area highlighted.

10. The method of claim 1, wherein the endoscope further comprises a motion sensing device to measure camera motion inside the human lumen.

11. The method of claim 10, wherein the motion sensing device corresponds to an accelerometer or a gyrator.

12. The method of claim 10, wherein the motion sensing device is used to determine camera movement, camera trajectory, camera orientation or any combination thereof.

13. The method of claim 12, wherein said mosaicking the regular images is performed in a space based on the camera trajectory.

14. The method of claim 1 further comprising generating a 2D or 3D mosaicked image and storing the 2D or 3D mosaicked image.

15. The method of claim 14, wherein the endoscope corresponds to a tethered endoscope and information of the 2D or 3D mosaicked image stored is used by an operator during withdraw process of the endoscope to re-image any missed area.

16. The method of claim 14, wherein the endoscope corresponds to a tethered endoscope and information of the 2D or 3D mosaicked image stored is used in a subsequent colonoscopy of a same patient.

17. The method of claim 1, wherein when a target area in the regular images is lack of parallax, the target area is determined as one missed area and an edge corresponding to a structure of the human lumen is highlighted.

18. The method of claim 17, wherein the endoscope is configured to be controlled or steered to move so as to re-image other side of the edge.

19. The method of claim 1, wherein when a target area in the regular images is lack of parallax, the target area is determined as one missed area and a related structure in the human lumen is highlighted.

20. The method of claim 19, wherein the endoscope is configured to be controlled or steered to move so as to re-image the target area.

21. The method of claim 1, wherein when a target area in the regular images is lack of a surface area in the mosaicked image, the target area is determined as one missed area.

22. The method of claim 1 further comprises deriving camera position, camera movement, camera orientation or a combination thereof inside the human lumen by using motion estimation based on the regular images.

23. The method of claim 1, wherein the endoscope corresponds to a tethered endoscope.

24. The method of claim 1, wherein the endoscope corresponds to a capsule endoscope.

25. The method of claim 24, wherein the endoscope is configured to be controlled or steered to move so as to re-image a detected missed area.

26. The method of claim 1 further comprising determining aggregated redundant areas in the regular images and reducing frame rate of the regular images if the aggregated redundant areas exceed a threshold.

27. The method of claim 1 further comprising increasing frame rate of the regular images if detected missed areas exceed a threshold.

28. A non-transitory computer-readable medium having stored thereon a computer-readable code executable by a processor to cause the processor to:
receive regular images captured by a camera while an endoscope travels through a human lumen;
mosaic the regular images into a mosaicked image to determine any missed area in a section of the human lumen travelled by the endoscope, wherein distance information of the regular images is used to assist said mosaicking the regular images, and the distance information is derived based on structured light images associated with the regular images, and wherein the regular images are normalized according to the distance information of the regular images and optical magnification information to facilitate said mosaicking the regular images; and
if any missed area is detected, provide information regarding any missed area.

* * * * *